United States Patent
Chelle et al.

(10) Patent No.: US 10,358,532 B2
(45) Date of Patent: Jul. 23, 2019

(54) METHOD FOR PRODUCING A NON-POROUS COMPOSITE MATERIAL THAT IS WATER-ABSORBENT AND LIPID-ABSORBENT FOR ACTIVE LIQUID COMPOSITIONS

(71) Applicant: AB7 INNOVATION S.A.S.U., Deyme (FR)

(72) Inventors: René Chelle, Grepiac (FR); David Nguyen, Toulouse (FR); Arnaud Vilbert, Baziege (FR)

(73) Assignee: AB7 Innovation S.A.S.U., Deyme (FR)

( * ) Notice: Subject to any disclaimer, the term of this patent is extended or adjusted under 35 U.S.C. 154(b) by 0 days.

(21) Appl. No.: 15/544,449

(22) PCT Filed: Jan. 20, 2016

(86) PCT No.: PCT/FR2016/000007
§ 371 (c)(1),
(2) Date: Jul. 18, 2017

(87) PCT Pub. No.: WO2016/116679
PCT Pub. Date: Jul. 28, 2016

(65) Prior Publication Data
US 2018/0265649 A1    Sep. 20, 2018

(51) Int. Cl.
| | |
|---|---|
| *C08J 3/12* | (2006.01) |
| *A01N 25/08* | (2006.01) |
| *A01N 25/12* | (2006.01) |
| *C08L 97/02* | (2006.01) |
| *B29B 9/16* | (2006.01) |
| *B29B 9/12* | (2006.01) |
| *A01N 37/40* | (2006.01) |

(52) U.S. Cl.
CPC ............... *C08J 3/12* (2013.01); *A01N 25/08* (2013.01); *A01N 25/12* (2013.01); *C08L 97/02* (2013.01); *A01N 37/40* (2013.01); *B29B 9/12* (2013.01); *B29B 9/16* (2013.01); *C08J 2300/16* (2013.01); *C08J 2303/00* (2013.01); *C08J 2389/00* (2013.01); *C08J 2397/02* (2013.01)

(58) Field of Classification Search
CPC ...... C08J 3/12; C08J 2300/16; C08J 2303/00; C08J 2389/00; C08J 2397/02; C08L 97/02; A01N 25/08; A01N 25/12; A01N 37/40
USPC ............................................................ 524/9
See application file for complete search history.

(56) References Cited

U.S. PATENT DOCUMENTS

2006/0263326 A1    11/2006  Weiser
2008/0293927 A1*  11/2008  Strahm .................. C08L 89/00
                                                                 530/500

FOREIGN PATENT DOCUMENTS

EP    0575838    12/1993
FR    2 959 100  10/2011

* cited by examiner

*Primary Examiner* — Hui H Chin
(74) *Attorney, Agent, or Firm* — McDonnell Boehnen Hulbert & Berghoff LLP

(57) ABSTRACT

The subject matter of the present invention is a method for producing a biodegradable, non-porous composite material made water-absorbent and/or lipid-absorbent, used for obtaining diversely shaped solid objects to be subsequently loaded with active liquid hydrophilic and/or lipophilic compositions comprising at least one active ingredient intended to be delivered into an environment in a controlled and continuous manner.

17 Claims, No Drawings

METHOD FOR PRODUCING A NON-POROUS COMPOSITE MATERIAL THAT IS WATER-ABSORBENT AND LIPID-ABSORBENT FOR ACTIVE LIQUID COMPOSITIONS

CROSS REFERENCE TO RELATED APPLICATIONS

This application is a U.S. national phase of International Application No. PCT/FR2016/000007, filed Jan. 20, 2016, which claims priority from and the benefit of French Application No. 1500117, filed Jan. 21, 2015. The entire disclosure contents of these applications are herewith incorporated by reference into the present application.

The present invention relates to the production of a biodegradable, non-porous composite material that is water-absorbent and/or lipid-absorbent for active hydrophilic or lipophilic liquid compositions.

More specifically, it relates to a method of producing a biodegradable, non-porous composite material that is made water-absorbent and/or lipid-absorbent, used for obtaining diversely shaped solid objects to be subsequently loaded with active hydrophilic and/or lipophilic liquid compositions comprising at least one active ingredient intended to be delivered into an environment in a controlled and continuous manner.

Active elements are commonly brought into some environments—air, soil or water—through various channels: air for volatile active elements, and direct contact for the active elements in liquid or solid form. This is the case, for example, in insect pest control by aircraft, in agricultural soil treatment by spreading or landfill, or in water treatment. To do this, said active elements are often incorporated into various supports to observe some environmental rules. Said supports, generally porous, are in the form of granules or pellets, impregnated with at least one active substance to be delivered into the target environment.

Indeed, for preserving nature from some aspects of environmental pollution, it is desirable to have the active ingredients released in controlled dose over time.

In the field of the invention, the supports for solid or liquid active substances are produced in various ways. Generally a porous support, in which the active composition will be incorporated, is produced. For example, this is the case of inoculum supported by shredded peat moss. This is also the case of patent FR2959100 B1 (Apr. 22, 2010) [AB7 Innovation] of the Applicant which discloses a method of porosification for biodegradable oil cake pellets, to impregnate with an active liquid lipophilic composition.

For the same purpose of making a structure porous to absorb active ingredients, Nadine LE BOLAY et al. [LGC ENSIACET-INP Toulouse, LCB, CIRIMAT-UMR CNRS] have developed a method for producing composite porous biodegradable materials for orthopedic use by co-grinding. In this case, the active ingredients are incorporated into the structure through a mineral load for modulating cellular activity after implementation.

One may also include in this category polymers made superabsorbent thanks to their porosity, that are put in a suspension for use in agriculture as disclosed by International Patent Application WO2009/014824 A2 (Jan. 29, 2009) [ABSORBENT TECHNOLOGIES, INC.], the polymers being obtained from starch and grafted starch.

Absorption pores may be specific to the structure of the material itself, or by acting on an existing material. However, they are often created during the production of the material. For this purpose, the skilled person uses various kinds of blowing agents. The idea is to remove said blowing agents, after shaping the objects to porosify, by various techniques that are adapted to the nature of the blowing agent that is used. For this purpose, a number of documents, dating from at least the last three decades, describe the application of these methods.

EP0012407 B1 (Dec. 10, 1978) [Parmit GmbH Porosierungsmittel für Baustoffindustrie (DE)] discloses a process for producing a blowing agent for the manufacture of porous shaped objects made of clay, in admixture with a powdered to fine-grained combustible material, with foam, and then granulated. This technology, based on the use of at least one blowing agent, is also used by the skilled person in different fields: EP0140757 A2 (Sep. 29, 1983) [HABIA CABLE SA] for the insulating layer of a coaxial cable; EP0784490 B1 (Oct. 3, 1995) [Cohesion Technologies, Inc.] for the production of biomedical implants with different properties of biodegradability; EP1000964 A1 (Nov. 5, 1999) [Institut Français du Pétrole] for developing cellular materials comprising at least one thermoplastic polymer, at least one modified epoxy resin and at least one blowing agent or the degradation product of said blowing agent; EP1436019 B1 (Dec. 16, 2001) [Biocomposites Limited Staffordshire] for a method of preparation of a biodegradable material for medical applications; EP1520593 B1 (Sep. 30, 2003) [ADC Dentall Advanced Care GmbH & CO KG] a method for producing a bone substitute material using at least one blowing agent; EP2228127A1 (Feb. 27, 2009) [Commission à l'Energie Atomique et aux Energies Alternatives] for a method of preparation of porous silica particles using a blowing agent that is soluble in water, said blowing agent being removed afterward by dissolution.

This technology is generally difficult to implement since using intrinsically porous materials requires a sterilization step or prior purification to remove undesirable elements found within the pores. Similarly, the use of blowing agents requires knowing how to remove them from the structure, an operation which can be complex and risky for the cohesion of the resulting porosified material.

More commonly, the person skilled in the art uses methods for incorporating both solid and liquid active substances directly into the support materials during the production of said materials. This is for example the claimed subject matter in some patent applications.

EP0529976 A1 (Aug. 22, 1991) [EI. DU PONT DE NEMOURS AND COMPANY] discloses a composition of particles for the slow release of herbicides, obtained by directly mixing: one to three herbicide compounds; paraffin wax; one or more natural or synthetic polymer(s) having a hydrocarbon backbone and particular solid filler. Said mixture is shaped by techniques known to those skilled in the art.

EP2226309 A1 (Mar. 4, 2009) [Daniela STERNINI] discloses an agricultural composition prepared by mixing directly: a superabsorbent polymer; a hygroscopic material of vegetal origin; a natural plasticizer and fertilizers and/or pesticides, and other additives commonly used in agriculture.

EP2718245 A1 (Jun. 13, 2011) [UAB «ARVI» ir ko] discloses a method for producing a granulated fertilizing mixture—nitrogen, phosphorus and potassium (NPK)—said mixture comprising solid components blended and ground in a mixer, wetted with water and/or steam, granulated, dried, fractionated in a blender and packaged.

It is also common to load the granules with active elements after they are shaped. This is for example the case in patent BRPI0817715 A2 (Sep. 30, 2014) [OMS INVESTMENTS INC.] which discloses a particular method of preparing granules for weed control, wherein herbicide ingredients are applied to the surface of said granules by coating. The granule, of which the base material has no active function, serves as a carrier which disintegrates when it becomes wet to release the herbicides.

To improve the homogeneity of the distribution of active elements in the supports according to the disclosed methods, the materials are pulverized into powder during mixing before the shaping of the finished products usually by granulation. Documents are cited as examples that describe this technology.

EP0880995 A2 (May 28, 1998) [Morimoto, Kiyoshi Shizuoka] discloses a method and a device for granulating powder material. This method which allows mixing the powder of the support material with the active solution prior to granulation is very complex. The same goes for the apparatus and method for producing pearl-shaped granules from a powder, described in EP0227508 A2 (Aug. 10, 1988) [DOW CHEMICAL CO]. The method and the system for powder granulation described in CA2844198 (27 Feb. 2014) [FORSYTHE & LONG INGINERING] also suffers from such complexity.

These methods of necessarily treating before granulation powders loaded with active compounds have several disadvantages. The methods are complex to implement. In addition to the complexity of their production process, said methods have the same technical drawbacks as those using the previously described blowing agents. All these methods provide finished products ready for use which, economically, have the significant disadvantage of not being adaptable to an unexpected request made by the user after the production of the loaded support, for a particular use or a change of the targets to reach. The loaded supports made with these technologies being restricted to a use for a specific purpose, the remaining products of a campaign, unused due to overproduction or because of an unexpected after-order change of targets, may have to be destroyed and simply amount to waste.

The object of the present invention is a method of producing a non-porous biodegradable composite material that is made water-absorbent and/or lipid-absorbent, used for obtaining diversely shaped solid objects to be subsequently loaded with active hydrophilic and/or lipophilic liquid compositions comprising at least one active ingredient intended to be delivered into an environment in a controlled and continuous manner, said method comprising the following steps:
  a) Select the base solid material or the mixture of a plurality of base solid materials of natural or synthetic origin;
  b) Mix the base solid material obtained in a) with the solid cohesion co-formulants or solid coabsorbants;
  c) Pulverize the mixture of solid materials obtained in b);
  d) Wet the mixture obtained in c) at a level between 9% and 13.5%;
  e) Add liquid cohesion co-formulants or liquid coabsorbants to the wetted mixture of
  d) to get a fine powder or a meal;
  f) Stock said fine powder or said meal obtained in e) for its maturation thereof;
  g) Shape said fine powder or meal obtained in f) into water-absorbent and/or lipid-absorbent non-porous solid objects;
  h) Stock the non-porous water-absorbent and/or lipid-absorbent solid objects obtained in g) in moisture-proof sealed containers;
  i) Subsequently incorporate at least one active liquid, or made liquid, composition, lipophilic or hydrophilic in said non-porous solid objects obtained in h) resulting in active solid objects;
  j) If applicable, coat the solid objects obtained in i);
  k) Stock the active solid objects obtained in i) or if applicable in j) in sealed containers.

Surprisingly, solid objects obtained from the non-porous composite material absorb hydrophilic and/or lipophilic active liquid compositions thanks to the addition of coabsorbants which form a network of water-absorbent and/or lipid-absorbent wicks in the mass of said material. Solid coabsorbants are biodegradable polymers, from a natural origin or not. They are selected from polysaccharides, natural gums, or a mixture thereof.

The method according to the invention is discontinuous, since it comprises storage steps which are partial interruption steps of the process. Indeed:
  Step f), for stocking fine powder or meal, is required for the maturation thereof which enables complete uniformity of liquid substance distribution in the powder mass;
  Step h), for stocking non-porous solid objects formed to promote flexibility in management of these intermediate products during loading operations of at least one liquid active composition that can vary for the same batch of objects produced.

The base solid materials used to obtain the material according to the invention are chosen from lignocellulosic, glucidic, or protidic biopolymers, either alone or in combination in natural or synthetic structures.

According to one aspect of the invention, the natural-origin materials are preferably derived from agro-industrial by-products. This is for example, without this list being exhaustive, of sunflower, soy and grape seed oil cake, and also coffee grounds, wheat bran, corncob, pulp beet, wheat flour, corn flour or processed animal proteins.

Natural base material for the production of the material according to the invention may be chosen from fibers from the textile industry that processes *miscanthus*, hemp or flax, this list not being exhaustive. Vegetal fibers are particularly useful in the consolidation of the composite material according to the method of the invention for obtaining objects having a high mechanical resistance.

According to an embodiment of the invention, the solid cohesion co-formulants are selected from binders such as vegetal resins, paraffins, natural gums such as xanthan, guar, cellulose derivatives, soy isolate, casein, gelatin, or the mixture thereof. They are used for the integrity and consolidation of the material during the shaping of the active solid objects from powder and/or meal base materials.

In order to optimize the mixture of solid materials as well as the homogeneous distribution of liquid materials into the mixture of solid materials, the solid materials are pulverized, the particle size varies between 1 micrometer and 3 millimeters, preferably between 10 micrometers and 500 micrometers.

Wetting of the mixture of solid materials according to the invention before pulverization is needed to make object shaping technically possible, particularly when using pressing methods that require a humidity of 9% 13% to provide sufficient plasticity for shaping the solid materials. Wetting is done taking into account the moisture already present in these solid materials to achieve rates between 9% and 13.5%.

According to the invention, the coabsorbants allowing the absorption by affinity of lipophilic active liquid compositions are selected from lipophilic liquids such as oils of vegetable origin or animal origin, or mineral oils, or a mixture thereof.

According to the invention, the coabsorbants allowing the absorption by affinity of hydrophilic active liquid compositions affinity are selected from amphiphilic liquid substances selected from glycerol, long-carbon chain alcohols or organic solvents commonly used and known to those skilled in the art, or mixture thereof compatible with the liquid active compositions and which do not participate in an increase of the moisture of the solids despite their hydrophilic character.

According to one embodiment of the object of the invention, one or more lipophilic coabsorbants and one or more hydrophilic coabsorbants can be mixed in the same structure which can thus absorb, with no preference, either hydrophilic active compositions and lipophilic active compositions or a mixture of thereof.

According to an advantageous aspect of the invention, the coabsorbants are intended for the formation of a network of lipophilic and/or hydrophilic wicks in the mass of the non-porous biodegradable composite material, thus making said material water-absorbing and/or lipo-absorbing, said wicks serving as penetration, distribution and release channels of the active liquid compositions in said non-porous biodegradable composite material.

According to a preferred embodiment of the invention, both the solid and liquid coabsorbants are added at levels ranging from 1% to 50%, by weight based on the total weight of the water-absorbing and/or lipo-absorbing non-porous biodegradable composite material, preferably between 5% and 50% by weight. The density of the absorbent wick network is proportional to the levels of added coabsorbants. It is the coabsorbants level that limits the amount of liquid active composition to be absorbed, this amount proportionally affecting the level and duration of delivery of said active composition. This limit is experimentally determined based on the nature of the non-porous biodegradable composite material, the nature of coabsorbants as well as the nature of the absorbed liquid active composition.

According to one embodiment of the invention, absorbent solid objects, depending on their use, can be shaped as pellets or granules of size ranging between 2 mm to 1 cm in diameter, and 2 millimeters to 4 centimeters long. They can also be shaped into plates from 10 cm to 1 meter of side, or polyhedral.

Shaping said objects according to the invention is carried out by high-pressure pressing, by thermopressing, by granulation pressing or granulation extrusion of the fine powder or meal, at temperatures taking into account the degradation temperature of the components of said fine powder or said meal.

Said water-absorbent and/or lipid-absorbent materials produced according to the method of the invention form a raw material that is storable and usable at will as needed to produce finished articles loaded with hydrophilic or lipophilic active liquid, or made liquid, compositions, and generally serving as controlled local release diffusers.

Loading the solid absorbing objects according to the invention with active liquid is done by various methods known to those skilled in the art, with the possibility to perform them in vacuum, namely:
  by spraying the active liquid composition on the absorbent solid objects by stirring the mixture, in a device that is preferably closed;
  by short-duration impregnation of the absorbent solid objects in the active liquid composition by successive additions of small amounts of said active liquid composition in the stirring device for impregnation.

Amounts of active liquid composition containing at least one active ingredient absorbed in the absorbing solid objects according to the embodiment of the invention vary from 5% to 50% by weight relative to the weight of the active solid object.

Advantageously, the active liquid composition containing at least one active ingredient absorbed into the solid objects according to the invention is thus protected from different physical, chemical or biological effects. It remains stable, both in quality and quantity, during the storage of said active solid objects, ensuring high reliability in use.

The active liquid compositions contain at least one active ingredient dissolved in a lipophilic or hydrophilic solvent. Depending on the required functionality according to the invention, said active ingredients are selected from fertilizers, biostimulants, plant protection substances, herbicides, biocides, fungicides, bactericides, insecticides, insect repellents, attractants, repellents, pheromones, antiparasitics, anti-pest, rodenticides, fragrances, essential oils, plant extracts, or a mixture thereof.

The active liquid composition incorporated in the active object made of a non-porous material rendered water-absorbent and/or lipid-absorbing according to the method of the invention, will be released by the active object at a controlled rate and continuously. The release rate of the active composition is a function of the level of "wicks" in the mass of the composite material, the level of said active composition incorporated therein and the nature of the ingredient(s) comprised therein. Indeed, according to one embodiment of the invention, the active ingredients may be heavy molecules which can only be released by the material at the migration rate of the dissolution medium, while volatile molecules will be released more rapidly by evaporation on the surface of the support. Thus, according to another embodiment of the inventive method, the active object with such small molecules is preferably coated in a thin layer of a substance having a melting point between 35 and 80° C., to better control the release rate. This substance is selected from solid paraffins at room temperature, natural waxes, hydrogenated vegetable oils, vegetable or animal fats or hydrophilic synthetic or natural long chain polymers (polyethers). The presence of hydrophilic and/or lipophilic wicks in the mass of the material does not change its biodegradability.

The finished products obtained by the method of the invention have high hardness and impact resistance, which is explained by the fact that handling them produces only between 2% and 10% by weight of fine particles, more commonly between 2% and 5% by weight for granules. However, the platelets produce almost none. The fine particles are the powder of material due to friction between the objects. Resistance of the active objects may be enhanced by coating them with solidified fat.

According to one aspect of the invention, the resulting objects have diverse functionalities selected specifically for the purpose of their use. They are therefore used in agriculture, food, veterinary medicine, breeding, animal feed, hygiene, perfumery, ambient air treatment or maintenance of green spaces.

EXAMPLE 1

I. Formulation of the Composite Material
   a) Sunflower oil cake, as a base solid material, is micronized in a blender;
   b) 870 grams of micronized sunflower oil cake, having 9% moisture, are introduced into a reactor;
   c) After stirring at 500 rpm for 5 minutes, 29.6 grams of water was added thereto in small doses for further wetting to 12% moisture, under constant stirring for 5 minutes;
   d) 100 grams of glycerol as a first coabsorbant are added thereto, under constant stirring for 5 minutes;
   e) 1 gram of castor oil as a second coabsorbant is added drop by drop, under constant stirring;
   f) The mixture is stirred for a further 5 minutes, to obtain powder that is stored in a sealed container.

II. Manufacturing Cylindrical Pellets
   a) The powder obtained in 1.f is placed in the feed hopper of a vertical die granulating press (14-175, Amandus Kahl) with a PW36 compression ratio;
   b) Pressing is performed with roller rotation set at 40% of maximum speed and a height of cutting blades set at 3 cm to obtain cylindrical pellets of 1 centimeter long and 6 millimeters in diameter;
   c) The granules obtained are stored in a sealed container.

III. A Posteriori Incorporation of the Active Ingredient in the Granules: Methyl Salicylate
   a) 85 grams of granules obtained in the preceding stage are introduced into a glass oil bath reactor, stirred at 500 rpm and at a temperature maintained at 65° C.;
   b) 15 grams of methyl salicylate (Reagent Plus >99%, Sigma Aldrich) is sprayed into the reactor under constant stirring, for 5 successive sequences separated by a pause;
   c) the reactor is kept under constant stirring at 200 rpm until the complete incorporation of methyl salicylate. Heating is turned off at the end of one hour for cooling to room temperature;
   d) the granules are then screened through a metal sieve of 2.8 mm mesh size. The fine particles are evaluated and weighed. They are evaluated at 3.1% of the total mass of the active ingredient-loaded product;
   e) then the active granules obtained are stored in a sealed container.

EXAMPLE 2

I. Formulation of the Composite Material
   a) 900 grams of processed animal protein (PAP Category 3) containing 10% moisture, as base solid materials, are mixed in a blender with 50 grams of grape seed oil cake containing 11% moisture as a solid co-formulant, and the mixture is micronized;
   b) The solid micronized mixture obtained in a) is placed in a reactor;
   c) After stirring at 500 rpm for 5 minutes, 50 grams of liquid digestate with 4% dry matter are added in small doses as a humectant, under constant stirring for 5 minutes;
   d) 100 grams of glycerol as a first coabsorbant are added thereto under constant stirring for 5 minutes;
   e) 1 gram of rapeseed oil as a second coabsorbant is added drop by drop, under constant stirring;
   f) The mixture is stirred for a further 5 minutes, to obtain powder that is stored in a sealed container.

II. Manufacturing Cylindrical Pellets
   a) The powder obtained in 1.f is placed in the feed hopper of a vertical die granulating press (14-175, Amandus Kahl) with a PW38 compression power;
   b) Pressing is performed with roller rotation set at 40% of maximum speed and a height of cutting blades set at 3 cm to obtain cylindrical pellets of 1 centimeter long and 6 millimeters in diameter;
   c) The granules obtained are stored in a sealed container.

III. Incorporation of Liquid Digestate as Active Composition into the Granules
   a) 70 grams of granulates obtained in the preceding step are introduced into a glass reactor stirred at 500 rpm;
   b) 30 grams of liquid digestate are sprayed into the reactor under constant stirring, for 5 successive sequences separated by a pause;
   c) the reactor is kept stirred at 200 rpm until complete incorporation of the digestate;
   d) the granules are then screened through a sieve of 2.8 mm mesh size. The fine particles are collected and weighed. They are evaluated at 4.1% of the total mass of the active ingredient-loaded product;
   e) then the active granules obtained are stored in a sealed container.

The invention claimed is:

1. A method of making a non-porous biodegradable composite material that is made water-absorbent and/or lipid-absorbent for obtaining diversely shaped solid objects and to be subsequently loaded with a hydrophilic liquid composition or a lipophilic liquid composition comprising an active ingredient intended to be delivered into an environment in a controlled and continuous manner, comprising:
   (a) selecting a base solid material or a mixture of a plurality of base solid materials, wherein the base solid material comprises lignocellulosic, glucidic, or protidic biopolymers of natural or synthetic origin;
   (b) mixing the base solid material or the mixture of a plurality of base solid materials with a solid cohesion co-formulant or a solid coabsorbant;
   (c) pulverizing a mixture of solid materials obtained in step (b);
   (d) wetting the mixture obtained in step (c) at a moisture level between 9% and 13.5%;
   (e) adding a liquid cohesion co-formulant or a liquid coabsorbant to the wetted mixture obtained in step (d) to get a fine powder or a meal;
   (f) stocking the fine powder or the meal obtained in step (e) for maturation thereof;
   (g) shaping the fine powder or meal obtained in step (f) into water-absorbent and/or lipid-absorbent non-porous solid objects;
   (h) stocking the non-porous water-absorbent and/or lipid-absorbent solid objects obtained in step (g) in moisture-proof sealed containers;
   subsequently incorporating the lipophilic liquid composition or the hydrophilic liquid composition in the non-porous solid objects obtained in step (h) resulting in a solid object;
   (j) optionally, coating the solid object obtained in step (i); and
   (k) stocking the solid object obtained in (i) or if applicable in (j) in a sealed container;

wherein the active ingredient is a fertilizer, a biostimulant, a plant protection substance, a herbicide, a biocide, an insecticide, an insect repellent, an attractant, a repellent, a pheromone, an antiparasitic, an anti-pest, a rodenticide, a fragrance, an essential oil, a plant extract, or a mixture thereof.

2. The method of claim 1, wherein the lignocellulosic, glucidic, or protidic biopolymers are free or are in association in natural or synthetic structures.

3. The method of claim 1, wherein the base solid material is an agro-industrial by-product chosen from sunflower, soy oil cake, grape seed oil cake, corncob, coffee grounds, wheat bran, pulp beet, wheat flour, corn flour, processed animal proteins or a mixture thereof.

4. The method of claim 1, wherein the base solid material is a vegetal fiber from *miscanthus*, hemp, flax or a mixture thereof.

5. The method of claim 1, wherein the solid cohesion co-formulant is a vegetal resin, a paraffin, a natural gum, a cellulose derivative, a soy isolate, a casein, a gelatin or a mixture thereof.

6. The method of claim 1, wherein the solid coabsorbant is a biodegradable polymer, of a natural origin or not, having an affinity with the hydrophilic liquid composition or the lipophilic liquid composition to absorb.

7. The method of claim 1, wherein the solid coabsorbant is a polysaccharide, a natural gum or a mixture thereof.

8. The method of claim 1, wherein the coabsorbant is a liquid amphiphilic substance selected from glycerol, a long-carbon chain alcohol compatible with the hydrophilic liquid composition or the lipophilic liquid composition to absorb or a mixture thereof.

9. The method of claim 1, wherein the coabsorbant is a liquid lipophilic substance selected from an oil of a vegetal or animal origin, a mineral oil or a mixture thereof.

10. The method of claim 1, wherein the coabsorbant is added into the powder or meal at a level between 1% and 50% by weight relative to the total weight of the non-porous biodegradable composite material.

11. The method of claim 1, wherein the coabsorbant is intended to form a network of hydrophilic and/or lipophilic absorbing wicks in the mass of the non-porous biodegradable composite material.

12. The method of claim 1, wherein the hydrophilic and/or lipophilic wicks serve as penetration channels for the hydrophilic liquid composition or the lipophilic liquid composition into the non-porous biodegradable composite material.

13. An object for delivering an active ingredient into an environment, made of a water-absorbent and/or lipid-absorbent non-porous biodegradable composite material obtained from the method of claim 1, wherein the object is shaped as granules of sizes varying between 2 millimeters and 1 centimeter in diameter and 2 millimeters and 4 centimeters in length.

14. The object of claim 13, wherein the object is shaped as plates with edges from 10 centimeters to 1 meter of side, or polyhedral.

15. The object of claim 13, wherein the object is loaded with an hydrophilic liquid composition or a lipophilic liquid composition comprising an active ingredient chosen from a fertilizer, a biostimulant, a plant protection substance, a herbicide, a biocide, an insecticide, an insect repellent, an attractant, a repellent, a pheromone, an antiparasitic, an anti-pest, a rodenticide, a fragrance, an essential oil, a plant extract, or a mixture thereof.

16. The object of claim 13, wherein the hydrophilic liquid composition or lipophilic liquid composition absorbed is at a level of between 5% and 50% by weight relative to the weight of the object.

17. A method of delivering at least one active ingredient into an environment in a controlled and continuous manner comprising using the object of claim 13 in agriculture, human or animal feeding, breeding, veterinary medicine, hygiene, perfumery, ambient air treatment, or maintenance of green spaces.

* * * * *